United States Patent
Guldi et al.

(10) Patent No.: US 7,024,950 B2
(45) Date of Patent: Apr. 11, 2006

(54) METHOD FOR INTELLIGENT SAMPLING OF PARTICULATES IN EXHAUST LINES

(75) Inventors: Richard L. Guldi, Dallas, TX (US); J. Michael Grobelny, Houston, TX (US)

(73) Assignee: Texas Instruments Incorporated, Dallas, TX (US)

( * ) Notice: Subject to any disclaimer, the term of this patent is extended or adjusted under 35 U.S.C. 154(b) by 534 days.

(21) Appl. No.: 09/982,656

(22) Filed: Oct. 18, 2001

(65) Prior Publication Data

US 2002/0062701 A1 May 30, 2002

Related U.S. Application Data

(60) Provisional application No. 60/250,399, filed on Nov. 30, 2000.

(51) Int. Cl.
*G01N 1/22* (2006.01)
*G01N 1/40* (2006.01)
*G01N 15/06* (2006.01)
*G01N 15/00* (2006.01)
*H01L 21/66* (2006.01)

(52) U.S. Cl. ............... 73/863.01; 73/28.01; 73/863.86; 438/5; 438/14

(58) Field of Classification Search ............ 73/863.23, 73/863.86, 28.04, 863.57, 865.5, 863.01, 73/28.01; 438/5, 14
See application file for complete search history.

(56) References Cited

U.S. PATENT DOCUMENTS

| | | | | |
|---|---|---|---|---|
| 3,217,549 A | * | 11/1965 | Cordell et al. | ............ 73/863.86 |
| 3,578,404 A | * | 5/1971 | Tousignant et al. | ............ 436/34 |
| 5,287,725 A | * | 2/1994 | Zhao et al. | ................... 73/23.2 |
| 5,421,048 A | * | 6/1995 | Reinert, Sr. | ..................... 8/158 |
| 5,652,966 A | * | 8/1997 | Reinert, Sr. | ..................... 2/457 |
| 5,654,205 A | * | 8/1997 | Chae et al. | .................... 438/14 |
| 5,856,623 A | * | 1/1999 | Ahn et al. | ............... 73/863.03 |
| 5,882,378 A | * | 3/1999 | Tarutani et al. | .................. 95/8 |
| 5,914,607 A | * | 6/1999 | Ju et al. | ..................... 324/439 |
| 5,963,336 A | * | 10/1999 | McAndrew et al. | ...... 438/16 X |
| 5,986,747 A | * | 11/1999 | Moran | ...................... 438/16 X |
| 5,996,420 A | * | 12/1999 | Lee | .................... 73/863.03 X |
| 6,082,179 A | * | 7/2000 | Jeon et al. | .................. 73/28.04 |
| 6,164,299 A | * | 12/2000 | Sun et al. | ............ 73/863.84 X |
| 6,591,201 B1 | * | 7/2003 | Hyde | .......................... 702/45 |
| 6,615,679 B1 | * | 9/2003 | Knollenberg et al. | .. 73/28.01 X |
| 6,649,416 B1 | * | 11/2003 | Kauer et al. | ................. 436/164 |
| 6,887,710 B1 | * | 5/2005 | Call et al. | ...................... 436/53 |
| 2002/0112658 A1 | * | 8/2002 | Holder et al. | ................. 117/15 |

FOREIGN PATENT DOCUMENTS

| | | | | |
|---|---|---|---|---|
| JP | 61-202139 | * | 9/1986 | ................ 73/865.5 |
| JP | 63-238445 | * | 10/1988 | .............. 73/863.33 |
| JP | 1-261832 | * | 10/1989 | |
| JP | 2000-88717 | * | 3/2000 | |

* cited by examiner

*Primary Examiner*—Thomas P. Noland
(74) *Attorney, Agent, or Firm*—Yingsheng Tung; Wade James Brady, III; Frederick J. Telecky, Jr.

(57) ABSTRACT

An in-situ particle monitor in an exhaust controls a particle sampler so that when a predetermined particle threshold is detected, the particle sampler is caused to gather samples from the exhaust in real-time. Electrical control signals are monitored to correlate variations in the signals with particle excursions for both analysis and sample collection triggering.

12 Claims, 3 Drawing Sheets

METHOD FOR INTELLIGENT SAMPLING OF PARTICULATES IN EXHAUST LINES

This application claims priority under 35 USC § 119(e)(1) of provisional application No. 60/250,399 filed Nov. 30, 2000.

BACKGROUND AND SUMMARY OF THE INVENTION

The present invention relates to integrated circuit structures and fabrication methods, and more particularly to improving yield analysis by monitoring exhaust products.

BACKGROUND

Particulates are a persistent plague in practical wafer processing. Most useful deposition or etch processes have some tendency to generate unwanted solid particles; unless such particles are significantly smaller than the minimum dimension of the integrated circuit structures, they are always a potential source of defects. For example, in a deposition process, some small fraction of the material being deposited may nucleate in the vapor phase to form free particles, or may nucleate on the chamber walls to form particulates which can be dislodged later by (e.g.) random vibrations, radiant heating, and/or ultraviolet illumination. In an etch process, some of the etch product may undergo secondary reactions to form solid particles. The transport of the wafer itself can generate free particles of the wafer material. The chamber itself can never be regarded as completely clean, and one of the considerations in designing the gas flow streams in a reactor is the inevitable entrained particulates (which preferably should exit with the flow of exhaust gasses, and not adhere to chamber walls or wafer surface).

The science of yield management is one of the most critical parts of semiconductor processing technology. Wafer fabrication processes are usually pushed to the ragged edge of engineering ability, so that yields may be, for example, well below 50% in a cutting-edge process, or above 90% in a highly refined process. Since a wafer with 10% yield is just as expensive (or cheap) to make as one with 90% yield, the yield is a key determinant of the economics of integrated circuit fabrication. The present application discloses new techniques and systems for yield management.

Due to the many sources of particulate generation, the density of particulates in the exhaust from a vacuum chamber is somewhat unpredictable. In-situ particulate monitors (ISPMs) can detect the presence of particles, but do not indicate the source of particles. This leaves characterization and source determination to further inquiry.

Intelligent Sampling of Particulates in Exhaust Lines

The present application discloses an innovative way to determine the particulate content of the exhaust from a process chamber. This allows the source of the particulates to be identified and eliminated if desired. The preferred embodiment uses an in-situ particle monitor placed in the exhaust line so that effluent content can be monitored. When the particle count exceeds a certain threshold (or upon some other predetermined event, such as a timing event) a particle sampling device is inserted into the exhaust stream. In the preferred embodiment, the particle sampling device comprises a moveable wand with a collector on the end. This collector can be easily removed and placed in an analysis tool, such as a SEM.

Advantages of the disclosed methods and structures, in various embodiments, can include one or more of the following:
improved particulate diagnosis by capturing the physical particle which causes the ISPM excursion;
reduced defect density in integrated circuits;
lower time to characterize and eliminate particle sources on equipment;
ease of transfer of particulates from sample collection to sample analysis;
ability to further differentiate particles by capturing only those particles exhausted during the exact time frame when the ISPM signal is abnormal.

BRIEF DESCRIPTION OF THE DRAWINGS

The disclosed inventions will be described with reference to the accompanying drawings, which show important sample embodiments of the invention and which are incorporated in the specification hereof by reference, wherein.

DETAILED DESCRIPTION OF THE PREFERRED EMBODIMENTS

The numerous innovative teachings of the present application will be described with particular reference to the presently preferred embodiment. However, it should be understood that this class of embodiments provides only a few examples of the many advantageous uses of the innovative teachings herein. In general, statements made in the specification of the present application do not necessarily delimit any of the various claimed inventions. Moreover, some statements may apply to some inventive features but not to others.

The present application is directed at improving yield analysis by identifying or characterizing the chemical composition of particulates in exhaust lines in order to diagnose the source of the particulates and to eliminate it. In one embodiment, this is done by the use of an in-situ particle monitor in the exhaust line. The ISPM (for example, an HYT model 70 sensor) monitors particle flux as a function of time. When particles are detected they can be sampled at that exact time. Other embodiments use different means to trigger collection of an exhaust sample, such as changes in the electrical control signatures of the process tool. These and other embodiments are discussed more fully below.

In a preferred embodiment, a collection wand is automatically inserted into the exhaust line when triggered by the ISPM. The ISPM will trigger the wand when the particle count exceeds a predetermined set point. Insertion of the collection wand at the precise time that the high effluent count is observed by the ISPM ensures that the desired particles, i.e. those observed by the ISPM, are collected. This allows the chemical composition of the particles in the exhaust to be analyzed so that the source of the particles may be diagnosed and eliminated. After sampling, the collection wand is transferred to a scanning electron microscope or other tool for chemical or physical analysis (depending on the analysis tool used).

The ISPM monitors the exhaust during the entire process, or any single phase of the process, as desired. For instance, a process might comprise wafer introduction into the chamber, chamber evacuation, preheating, turning on power, turning on gasses, turning on power to begin deposition, turning off power, turning off gases, ventilating the chamber, and unloading the wafer. The ISPM can be controlled to trigger sample collection at any change of particles in any or all of the phases of a process.

Figure 1:
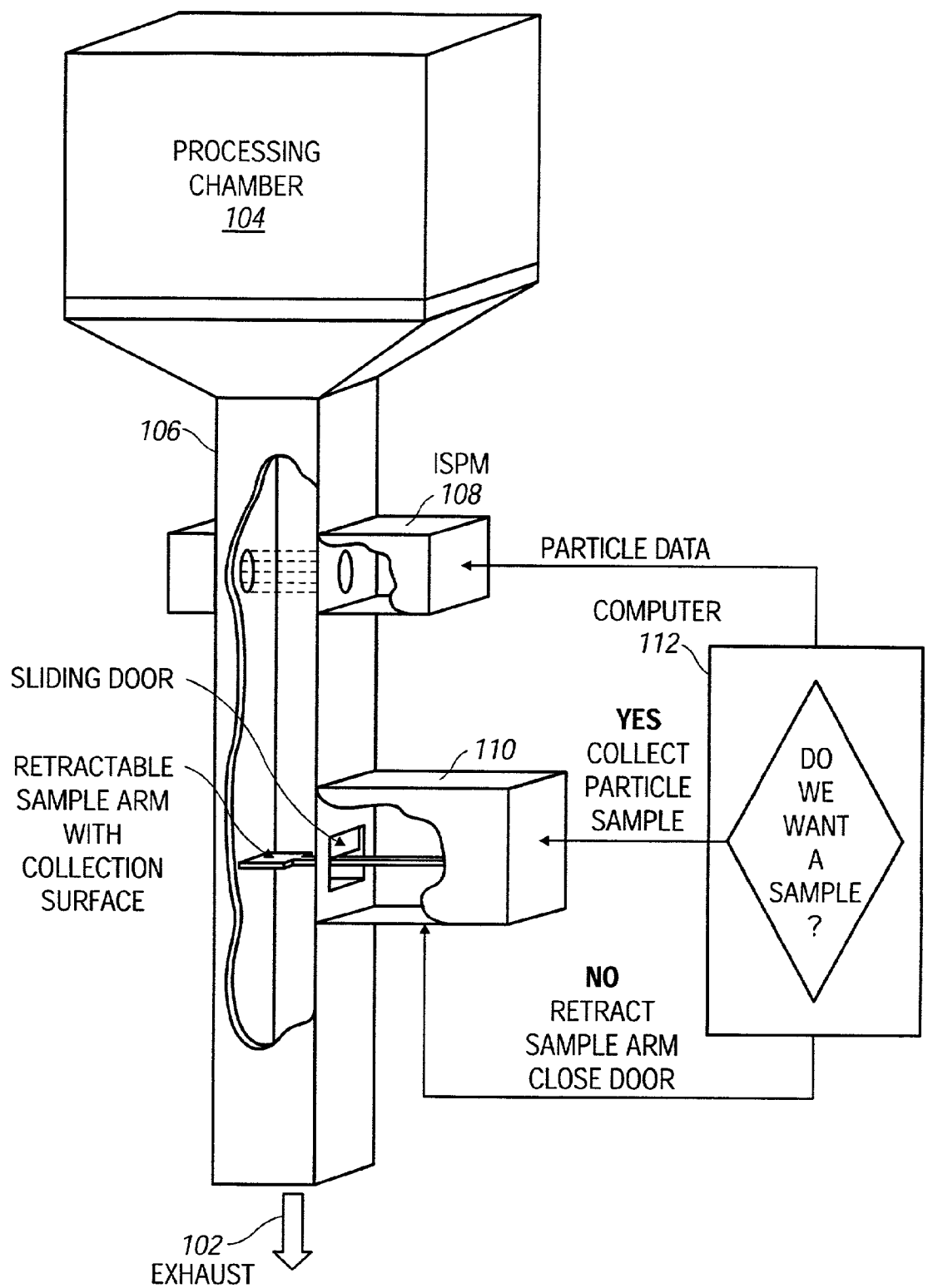
FIG. 1 shows a processing chamber and exhaust equipped with the innovative particle sampling system.

FIG. 1 shows a processing chamber with exhaust according to the preferred embodiment. Exhaust 102, possibly containing particulate produced in the process, flows from the processing chamber 104. Situated within the exhaust line 106 is an ISPM 108 which collects particle data monitoring particle flux as a function of time. Downstream of the ISPM 108 is a particle sampler 110 in the form of a wand with a collection surface at the end. The sample collector 110 can also be placed upstream, which might have the advantage of sampling particles that adhere to the walls and do not make it far from the chamber exhaust portal. The collection device can be extended into the exhaust or retracted into a housing, isolating it from the effluent by a sliding door. The wand placement might also vary, choosing to sample closer to the walls of the exhaust or the center.

Depending on the particular tool, the exhaust line can bend before or after the collector insertion point. This can affect the quality of the sample; since some particles will adhere to the walls and not travel well around corners.

In the preferred embodiment, the ISPM 108 sends the particle data to a computer system 112 that monitors the particle count. When the count exceeds a predetermined threshold, the computer 112 automatically extends the sampling device 110 so that the collection surface is exposed to the particles in the exhaust 102. After sufficient exposure (or after the particle count is reduced to below a predetermined threshold) the collection device is retracted into its housing. Any predetermined event can serve as the trigger, including high particle count, timing events, or the detection of an exhaust constituent that is desired to be analyzed.

Figure 2:
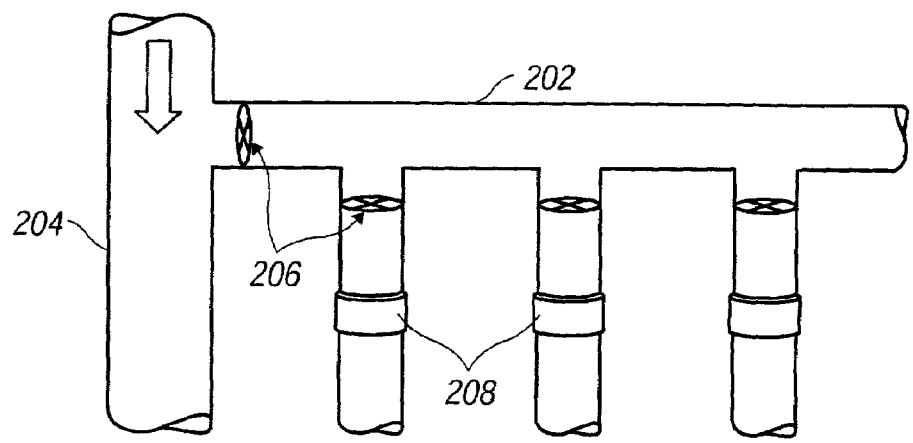
FIG. 2 shows a sampling mechanism for a wet bench according to a preferred embodiment.

FIG. 2 shows a sampling mechanism for a wet bench which represents a contemplated but less preferred embodiment. A sampling line 202 connects to a recirculation line 204 that contains effluent to be sampled. Valves 206 isolate the sampling line 202 and filter 208 housings from the recirculation line 204. These valves 206 are slaved to the ISPM (not shown), so that when the count exceeds a predetermined threshold (or upon a different specified triggering event) the valves 206 open allowing the flow to enter the sampling line 202. This allows the filters 208 (i.e., the sample collection devices) to be used at their most sensitive by not exposing them to the passing liquid until an excursion begins: Diversion of flow into a sampling region (instead of sampling the direct flow of exhaust from the chamber) can be done with either wet (liquid) or dry (gaseous) exhausts.

Figure 3:
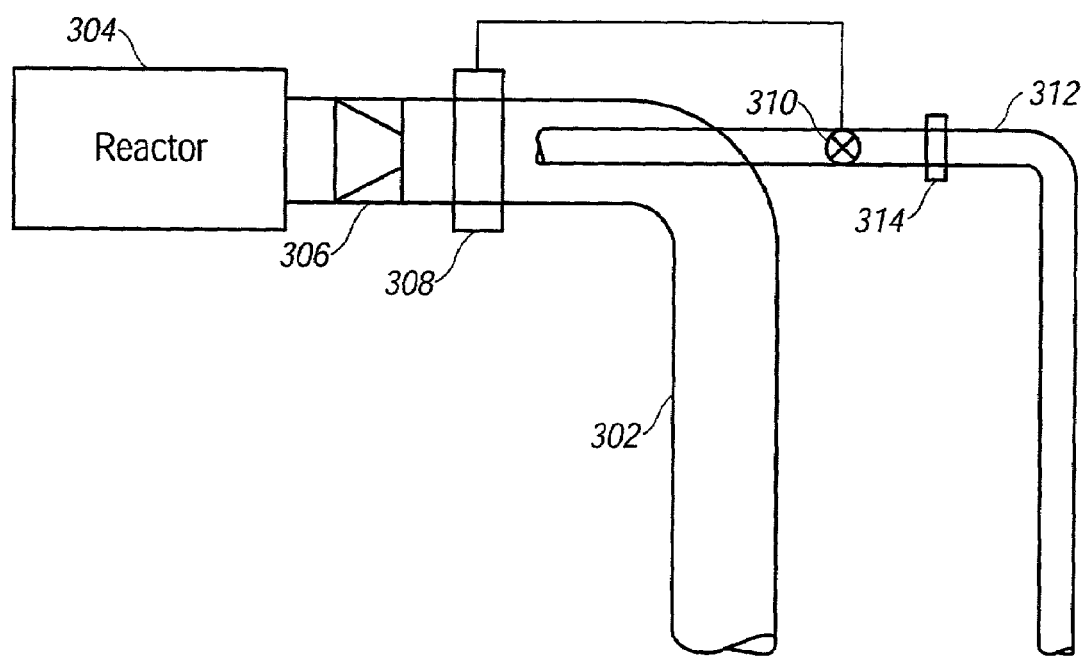
FIG. 3 shows an alternative embodiment of the innovative sampling system.

FIG. 3 shows an alternate sample collector design. An exhaust line 302 exits a reaction chamber 304. A baffle/sample concentrator 306 is located in the exhaust line 302. The baffle 306, if used, focuses the solid particles to the center of the exhaust pipe, and can comprise a funnel shaped device or a straight tube. An ISPM 308 is located after the baffle 306 (though in other embodiments, the ISPM 308 may be located upstream of the baffle 306, if used) and is connected to trigger a valve 310 in a sample collection line 312. In this embodiment the collection line 312 is a straight pilot tube inserted into the exhaust flow. When the particle count exceeds a predetermined threshold (or at a specific timing event), the ISPM 308 will cause the valve 310 to open, allowing particulates to enter the sample collection line 312. The collection line 312 is in-line with the exhaust path so the particles have a straight path to the sample collector 314, decreasing the chance to lose particles to sidewall adhesion, for example.

The collector in the preferred embodiment uses a membrane filter, though other types of filters can be employed.

In the preferred embodiment, the wand insertion occurs precisely when the high level particle flux is detected. This allows the wand to collect particles from that particular source, avoiding extraneous particles that might otherwise occur at some point in the processing. The wand collection platform is designed to accommodate a minivac filter membrane or a silicon substrate which fits into a SEM or other analysis tool.

In the preferred embodiment, the collection wand is a moveable sampling arm that can be inserted into the exhaust line. Multiple arms may be provided to collect different samples activated by different timing events or ISPM thresholds. The wands can be stacked vertically, horizontally, arranged as the spokes of a wheel, or any other convenient configuration. The sampling devices may be permanently mounted to the equipment or may be removeable so as to be useable on different equipment, depending on the exact uses desired. A loadlocked version may be used in some embodiments for collecting and transporting special samples.

Figure 4:
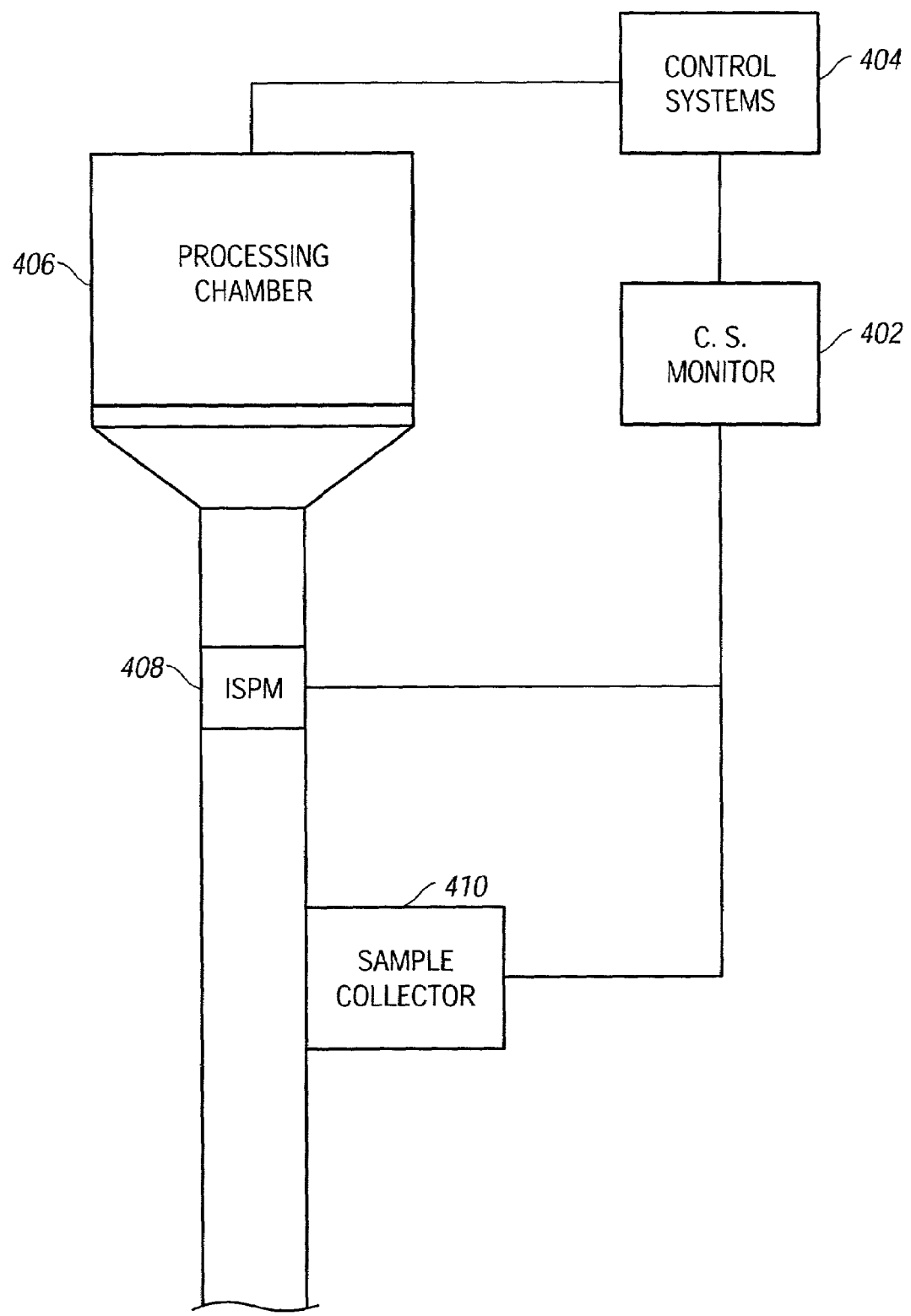
FIG. 4 shows a block diagram of an embodiment that monitors electrical systems of the process chamber.

FIG. 4 shows an embodiment that triggers sampling by monitoring one or several electrical control signatures of the process tool. A monitoring system 402 is connected to the electrical control systems 404 of the process chamber 406 and monitors an electrical control signature such as gas flow controller signals, forward power, reflected power, infrared emissions, or other signals. Any abnormality in the signature of the monitored system or systems triggers the collection of a sample by any of the various means discussed in other embodiments (e.g., collector 410). What qualifies as a triggering event could be defined as any fluctuation of the signature outside a threshold range of acceptable values, for example.

In another embodiment, the electrical control signal monitoring is used with an ISPM 408 monitoring particle flux. Whenever the ISPM 408 detects a particle, the signal of whatever system being monitored is noted and associated with the particle excursion. (Note, some other aspect of the process tools can be monitored, other than just the electrical control signatures. Changes in the gas flow controller signals, forward power, reflected power, infrared emissions or any other observable signal from the process tool such as optical emissions or endpoint detection indicators can be monitored as well.) By collecting samples and analyzing them, that type of signal variation that occurred at that time can be reliably associated with that particular type of particle excursion. In this way, a repertoire of signals can become associated with particle excursion so that monitoring the control signals provides more information for particulate analysis.

In the previous embodiment, the detection of a particle by the ISPM triggers particulate collection. In another embodiment, the electrical control signatures themselves can also be used to trigger collection (with or without an ISPM). For example, any signal variation that is already known to be associated with a particle excursion can be used to trigger sample collection.

Along these lines, the electrical control signal (or other signals that are monitored) monitors which are used to trigger sample collection can be "trained" to recognize the type of particle associated with a particular variation in control signature so that the cause of the particle excursion can be more easily diagnosed. After a sufficient repertoire of signal variations are associated with the proper causes of the variations, sample collectors and/or ISPMs need not be used. This is because, since the signature of the monitored control system has previously been determined to be caused by a given problem with the system, the mere detection of that signal variation can alert the tool's operator to the nature of the problem without the need to collect and analyze a particle sample from the exhaust.

For example, the control systems monitor can be used to monitor reflected power in the process chamber's electrical control system. In order to develop a repertoire of reflected power signatures that are correlated with a particular particle excursion, an ISPM and a sample collector are also used. When the ISPM detects an excursion, the collector collects a sample from the exhaust to be analyzed. The characteristics of the reflected power signal during (and/or before) the excursion is identified with that particle excursion (whatever analysis determines it to be). This continues, and each particle excursion causes collection and analysis, and the control signatures from each of the excursions are correlated to with their respective excursions.

Using this method, the control signals themselves become the indicators of the source of particle excursions because when a recognized variation in the monitored signal happens, the source of the excursion can be predicted from the variation itself, without the need to actually collect a sample. That variation in the signal is compared to the repertoire of known signals and their related types of particle excursion (which was developed using the above mentioned method). If the signal variation matches a known signal variation, the source of the particle excursion will also be known. (Note that this technique may or may not be accompanied by an ISPM and/or a collection device.)

In other embodiments, the signal monitor (which controls triggering of sample collection) can be connected to any type of detection device, such as an optical detector, if desired. Any observable on the process tool that is associated with a particle excursion, or is merely abnormal, or goes outside a threshold range, or exhibits any other identifiable characteristic, can be used to send the collection device into effect and to aid in analysis. This rapid feedback not only helps determine the probable cause of the excursion, but can also let the equipment user know when it is safe to continue using the tool.

These methods of sampling collect effluent from the exhaust at the precise time it is produced. By collecting the effluent on a sample holder that mounts on a scanning electron microscope or other analysis tool, the collected sample may be easily analyzed. This technique facilitates rapid problem solutions by providing information about the effluent necessary for elimination of the source.

This method of particulate sampling allows a sample to be collected real time and without disturbing the process or equipment. Once the sample is completed, either after a given amount of time or the particulate count returns to a baseline, the valves automatically close and the sample can be removed for immediate analysis. Analysis methods can vary and include SEM, EDS (Energy Dispersive Spectroscopy), ICP (Inductively Coupled Plasma analysis), or other analysis methods can be used.

The presently disclosed innovations allow superior particle collection and analysis, reducing the time to identify and eliminate particle sources in the wafer manufacturing process. The tool also assists in rapid resolution of defect excursions. Products will benefit from reduced defect density and lower times to eliminate particle sources on equipment.

Modifications and Variations

As will be recognized by those skilled in the art, the innovative concepts described in the present application can be modified and varied over a tremendous range of applications, and accordingly the scope of patented subject matter is not limited by any of the specific exemplary teachings given, but is only defined by the issued claims.

While the inventions have been described with reference to a single processing chamber with exhaust, it will be readily recognized that these innovations can be applied to processes using cluster tools or other multiple chamber configurations.

Likewise, the exact method of monitoring the effluent is not limited to the use of an ISPM, since other means of detecting exhaust content may exist or be developed in the future. Any method of triggering exhaust sampling is within the contemplation of the present application if it employs the innovative concepts herein described.

For instance, redirecting part of the exhaust, removal of the exhaust, or in-situ monitoring of the exhaust are all possible means of implementing the present innovations.

Likewise, different aspects of processing tool performance can be substituted for the electrical control systems which are monitored in some embodiments. For example, optical detectors placed to view relevant areas can be used to program or trigger the system.

The type of triggering mechanism can be automatic or might also be designed to require an extra step (such as operator intervention) before sampling is done.

Additional general background, which help to show the knowledge of those skilled in the art regarding variations and implementations of the disclosed inventions, may be found in the following documents, all of which are hereby incorporated by reference: Coburn, PLASMA ETCHING AND REACTIVE ION ETCHING (1982); HANDBOOK OF PLASMA PROCESSING TECHNOLOGY (ed. Rossnagel); PLASMA ETCHING (ed. Manos and Flamm 1989); PLASMA PROCESSING (ed. Dieleman et al. 1982); Schmitz, CVD OF TUNGSTEN AND TUNGSTEN SILICIDES FOR VLSI/ULSI APPLICATIONS (1992); METALLIZATION AND METAL-SEMICONDUCTOR INTERFACES (ed. Batra 1989); VLSI METALLIZATION: PHYSICS AND TECHNOLOGIES (ed. Shenai 1991); Murarka, METALLIZATION THEORY AND PRACTICE FOR VLSI AND ULSI (1993); HANDBOOK OF MULTILEVEL METALLIZATION FOR INTEGRATED CIRCUITS (ed. Wilson et al. 1993); Rao, MULTILEVEL INTERCONNECT TECHNOLOGY (1993); CHEMICAL VAPOR DEPOSITION (ed. M. L. Hitchman 1993); and the semiannual conference proceedings of the Electrochemical Society on plasma processing.

What is claimed is:

1. A fabrication method, comprising the steps of:
   monitoring the exhaust of a process chamber; and
   automatically sampling said exhaust when a particle excursion occurs.

2. The method of claim 1, wherein said step of monitoring is done using an in-situ particle monitor.

3. The method of claim 1, wherein said step of sampling is done by inserting a collection device into said exhaust.

4. The method of claim 1, wherein said exhaust is sampled by redirecting said exhaust to a sampling area.

5. The method of claim 1, wherein an electrical control signal of said process chamber is monitored and correlated to said event.

6. A fabrication method, comprising the steps of:
monitoring at least one signal of a process chamber; and
sampling the exhaust from said process chamber when detecting a given particle flux by an in-situ particle monitor located in said exhaust.

7. The method of claim 6, wherein said signal is an electrical control signal.

8. The method of claim 6, wherein the deleting occurs at a variation in said signal.

9. A wafer processing system, comprising:
a chamber with an exhaust;
a particle monitor located in said exhaust;
wherein said particle monitor is connected to cause a partide sampler to gather samples from said exhaust when a predetermined particle flux is detected.

10. The system of claim 9, wherein said sampler gathers samples by being inserted into said exhaust.

11. The system of claim 9, wherein said sampler gathers samples by opening valves so that said exhaust passes to a sampling area.

12. The system of claim 9, wherein said sampler is a membrane filter.

* * * * *